(12) United States Patent
Engelhardt

(10) Patent No.: US 10,398,878 B2
(45) Date of Patent: *Sep. 3, 2019

(54) MEDICAL TUBING AND CATHETER CONTROL

(71) Applicant: Bernard Engelhardt, Maple (CA)

(72) Inventor: Bernard Engelhardt, Maple (CA)

(73) Assignee: Bernard Engelhardt, Maple, Ontario (CA)

(*) Notice: Subject to any disclaimer, the term of this patent is extended or adjusted under 35 U.S.C. 154(b) by 174 days.

This patent is subject to a terminal disclaimer.

(21) Appl. No.: 15/217,373

(22) Filed: Jul. 22, 2016

(65) Prior Publication Data
US 2017/0021135 A1    Jan. 26, 2017

Related U.S. Application Data

(63) Continuation of application No. 13/173,346, filed on Jun. 30, 2011, now Pat. No. 9,427,552.

(60) Provisional application No. 61/359,912, filed on Jun. 30, 2010, provisional application No. 61/478,566, filed on Apr. 25, 2011.

(51) Int. Cl.
A61M 25/02    (2006.01)
A61F 5/44     (2006.01)
A61M 25/00    (2006.01)

(52) U.S. Cl.
CPC ............. A61M 25/02 (2013.01); A61F 5/44 (2013.01); A61M 25/0017 (2013.01); A61M 2025/024 (2013.01); A61M 2025/0206 (2013.01); A61M 2025/0266 (2013.01)

(58) Field of Classification Search
CPC ............. A61M 25/02; A61M 25/0017; A61M 2025/0206; A61M 2025/024; A61M 2025/0266; A61M 2025/0098; A61F 5/44
See application file for complete search history.

(56) References Cited

U.S. PATENT DOCUMENTS

| 4,531,245 A * | 7/1985 | Lowd | A47K 11/00 141/337 |
| 4,606,346 A * | 8/1986 | Berg | A61F 5/34 606/196 |
| 4,979,505 A * | 12/1990 | Cox | A61M 16/04 128/207.15 |
| 7,325,256 B1 * | 2/2008 | Pecinka, Sr. | A61F 5/4556 4/144.1 |

(Continued)

Primary Examiner — Adam Marcetich
(74) Attorney, Agent, or Firm — Perry + Currier Inc.

(57) ABSTRACT

One embodiment is an improved method for providing a tube for attachment to a medical device such as a catheter that provides for intermittent changes in tube path length as a result of body movement thereby reducing the stress and pain caused by pulling on the device, as well as the optional provision to provide a very low, controlled tension that provides improved stability of the medical device without damage to the surrounding body tissues. This controlled tension can be applied or removed intermittently by a medical practitioner or the patient. The tubal devices shown in Fig and Fig both provide for extension in tubal path length while simultaneously providing for intermittent or continuous low tension pull on the catheter. Provision is also made for a continuous smooth fluid path with no moving internal parts.

12 Claims, 13 Drawing Sheets

(56) References Cited

U.S. PATENT DOCUMENTS

| | | | | |
|---|---|---|---|---|
| 2005/0267442 A1* | 12/2005 | Von Oepen | ....... | A61M 25/0021 604/509 |
| 2006/0271019 A1* | 11/2006 | Stoller | ...................... | A61F 5/44 604/544 |
| 2007/0208314 A1* | 9/2007 | Barrientos | ................ | A61F 5/44 604/353 |
| 2007/0213661 A1* | 9/2007 | Gobel | ................... | A61F 2/0013 604/96.01 |
| 2007/0225688 A1* | 9/2007 | Goodwin | .............. | A61F 5/4404 604/544 |
| 2008/0167542 A1* | 7/2008 | Lampropoulos | ........ | A61B 90/06 600/345 |
| 2008/0172040 A1* | 7/2008 | Smith | ............... | A61M 25/0017 604/544 |
| 2009/0177183 A1* | 7/2009 | Pinkernell | ............. | A61M 25/00 604/506 |
| 2009/0198107 A1* | 8/2009 | Park | ....................... | A61B 17/02 600/215 |
| 2010/0094173 A1* | 4/2010 | Denton | .............. | A61M 1/0043 600/584 |
| 2011/0087181 A1* | 4/2011 | Bidwell | ................ | A61F 5/4404 604/328 |

* cited by examiner

MEDICAL TUBING AND CATHETER CONTROL

CROSS-REFERENCE TO RELATED APPLICATIONS

This application claims the benefit of U.S. provisional patent application No. 61/359,912 filed Jun. 30, 2010 and U.S. provisional patent application No. 61/478,566 filed Apr. 25, 2011.

BACKGROUND

1. Field of Invention

This invention relates to fluid handling lines and their attachment to catheters or other medical devices, more specifically to tube length compensation features that help to stabilize and isolate the catheter or other medical devices.

2. Prior Art

There are many areas in the medical field where a fluid handling tube is attached to a device fastened onto or into the body. Problems arise that are the result of body movements that alter the length of the tubal path, instances where the tube is subjected to sudden hard tugs, and movement of the device itself as a result of skin movement even when fastened down with adhesive tape. In cases where the device is a catheter, whether urinary, IV, or other, the movement caused and the forces exerted may cause damage to the organ or vein as well as actual dislodgement of the catheter In the case of urinary catheters, which are flexible tubes, usually made of Latex or a Latex blend, that are passed through the urethra and into the bladder. The catheter is retained inside the bladder by means of a balloon, located at the inserted end, which is inflated with sterile water. The diameter of the inflated balloon is greater than the internal diameter of the urethra. The external end of the catheter is attached to a drainage tube which leads to a drainage (or collection) bag. The drainage tube is usually secured to the leg of the patient in order to help control wild swings in the tubing and the resultant effects on the catheter. Care must be taken, when securing the drainage tube to the leg, to ensure a sufficient length of tubing is available to form a loop. If not enough slack tubing is available, the patient risks damaging their bladder if they stretch their leg too far. This configuration, however, creates another problem. The inflated balloon prevents the catheter from accidentally being pulled out of the bladder, but there is nothing restricting the catheter from moving further into the bladder. Because of the extra length of tubing loop between the connection point on the leg and the catheter balloon, the catheter balloon is free to move within the bladder, and will move every time the patient's leg moves. This movement causes both discomfort and irritation and, as a result, an increased risk of infection. When the catheter moves in far enough, the top of the catheter will bump against the bladder top. This is thought by many to be a cause for bladder spasms, a very painful condition. As the catheter moves back down, such as when the leg is stretched sideways, the tubing will pull out the catheter until the balloon rests on the bottom of the bladder. The pulling in and pushing out, or pistoning, of the catheter, causes irritation of the urethra, but more significantly, increases the risk of catheter associated urinary tract infections.

Current state of the art for urinary catheter securement is a device, which can secure the catheter directly to the thigh, but can be shown to be self defeating. In this case, the catheter itself is fastened to the thigh thus guaranteeing that the catheter will piston in and out with every leg movement. If placed improperly, severe bladder damage may result.

According to the Centers for Disease Control and Prevention (CDC) website, each year, 30,000,000 urinary catheters are inserted into over 5 million patients in acute care hospitals and extended care facilities in the U.S. alone. Up to 25% of these patients, over one million per year, develop catheter associated urinary tract infection (CAUTI), when requiring catheterization for at least 7 days; the daily risk is 5%. CAUTI is the most common nosocomial infection, and the second most common cause of nosocomial blood stream infection. Studies suggest that patients who have developed CAUTI have an increased institutional death rate, unrelated to the development of urosepsis. As the population grows in size and in age, and the average life expectancy rate increases, each year more and more people will require catheterization. This along with the unwillingness, of a growing number of health insurance companies, to pay hospitals for nosocomial infection treatment, creates an urgent need for a solution.

SUMMARY OF THE INVENTION

To effectively reduce the discomfort and risk of infection caused by the use of a Foley catheter, a controlling device is needed to compensate for the changes in the length of the drainage tube path, as the distance from the catheter to the attachment point on the thigh changes. In this way, there is no need for a free loop of slack drainage tubing. The free loop causes an increase in pistoning, as the loop swings and changes size with the patient's movement. The free loop can also get caught on clothing resulting in a substantial pull on the catheter, which can damage the catheter as well as the patient's bladder and/or urethra. All of these movements further increase the irritation on the penis tip.

To further reduce pistoning, the controlling device described herein could provide a continuous, but minimal pull (minimal pull is that force great enough to hold the catheter balloon at the bottom of the bladder, but not great enough to cause damage to the blood vessels and tissue on the bladder bottom if applied continuously, present approximation, subject to actual testing, is less than 3 ounces) on an engaged Foley catheter such that the balloon of the catheter will always be resting on the bottom of the bladder. This action, in conjunction with the means of compensating for the changes in the length of the drain tube path from the catheter to the attachment point on the thigh, will protect the bladder and the urethra from damage caused by a very strong pull on the catheter, such as occurs when the tubing catches on something or the leg movement causes an excessive pull as well as reducing the pistoning action in and out of the urethra. The urethra is further protected by reducing the pistoning of the catheter and the associated introduction of foreign matter that adheres to the moist catheter when it exits the urethra, and is re-introduced into the urethra when it re-enters with the accumulated debris, lint and fecal matter that has adhered to the moist catheter.

Furthermore, the said method is non-invasive and low cost. It could potentially save hospitals millions of dollars each year by reducing time and medication costs associated with the treatment of CAUTI, not to mention the savings of those lives that are already in a weakened state and could not withstand yet another infection.

DRAWINGS

Figure 1:
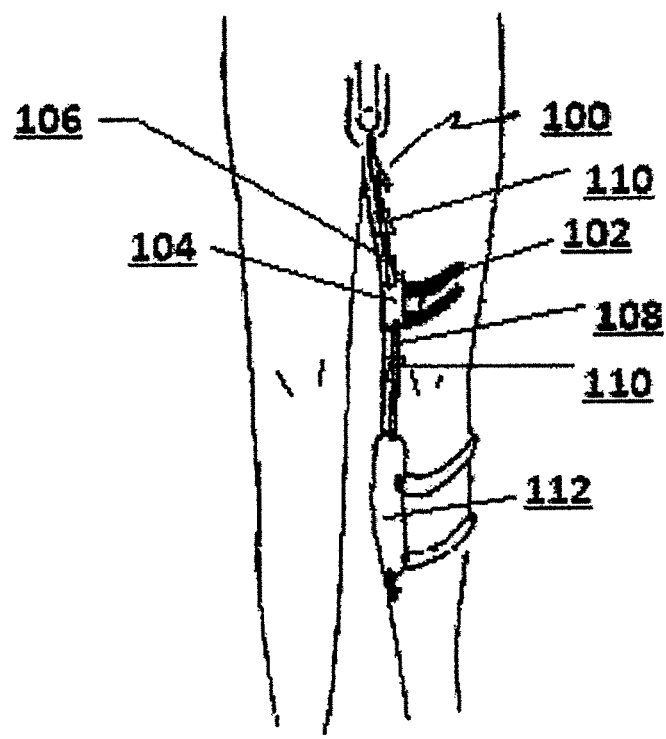
FIG. 1 shows a typical male Foley urinary catheter attached to a compensating device (or controller) with a connector. The compensating device is illustrated as being attached with adhesive tape to the thigh and the outgoing tube leading to a collection bag.

Reference Numerals
100—Foley catheter
102—attachment tape
104—compensating device
106—incoming tube
108—outgoing (or drainage) tube
110—tube connectors
112—collection bag
200—first embodiment
202—base
204—tube loop
206—connection to external end of catheter
208—connection to collection bag
210—tension spring (or elastic member)
212—cover plate
214—attachment of tube to base
215—bottom edge of base
216—underside surface of base
218—tube compartment
220—bottom section of base
302—calibration markings
304—direction of force by tension spring
306—direction of tension on Foley catheter
400—second embodiment
402—cover strap
404—adhesive section on cover strap
500—third embodiment
502—injection molded base
504—cover plate
506—living hinge
508—tube compartment walls
510A—snap fitting (male end)
510B—snap fitting (female end)
512—adhesive release holes/breathability holes
600—tension adjustment cam
602—recess for mounting post
604—attachment point of tension spring
606—recess for slide in un-tensioned position
608—recess for slide in tensioned position
610—dial handle
700—slide
702—compression spring (non-compressed)
702A—compression spring (compressed)
704—front of slide
706—slide handle
800—base for adjustable embodiment
802—post for mounting cam
804—dial compartment
806—slide compartment
808—rib for preventing drainage tube/tension spring contact
900—adjustable embodiment 902—cover for adjustable embodiment
904—cutout for dial handle
906—cutout for slide handle
1210—container
1212—tube bottom
1214—hole
1222—outgoing tube
1226—incoming tube
1228—bellows type section
1230—cap
1240—spring
1242—threaded section
1310—outer shell cover
1311—Outer Shell Exiting Cover End
1312—incoming tube
1313—outgoing tube
1314—elastomer tube (or elastic member)
1316—D-shaped slider
1317—outer shell exiting end hole
1319—outer shell incoming cover end 1322—stop projection
1324—outer shell cover end
1410—outer shell
1411—outer shell exit end
1412—incoming tube
1413—outgoing tube
1414—elastic tube (or elastic member)
1416—slider
1417—slider hole
1418—safety pin entry hole
1424—exiting hole
1430—outer shell bottom plate (base)
1432—slider stop
1434—inner shell stop
1440—inner shell
1442—inner shell back plate
1444—inner shell incoming hole
1446—inner shell maximum movement stop
1448—inner shell leading edge
1449—dotted line (secondary position)
1450—safety pin
1452—raised projection
1512—incoming tube
1514—elastic tube
1552—IV outer shell
1554—IV inner shell
1556—IV needle/catheter
1560—inner shell stop

DETAILED DESCRIPTION

First Embodiment

FIG. 1 shows a typical male Foley urinary catheter 100, inside the bladder with the incoming tube 106 leading to a compensating device 104 thru connector 110. The device 104 is attached to the thigh with adhesive tape 102. The outgoing tube 108 leads to the collection bag 112 thru a second connector 110.

Figure 2A:
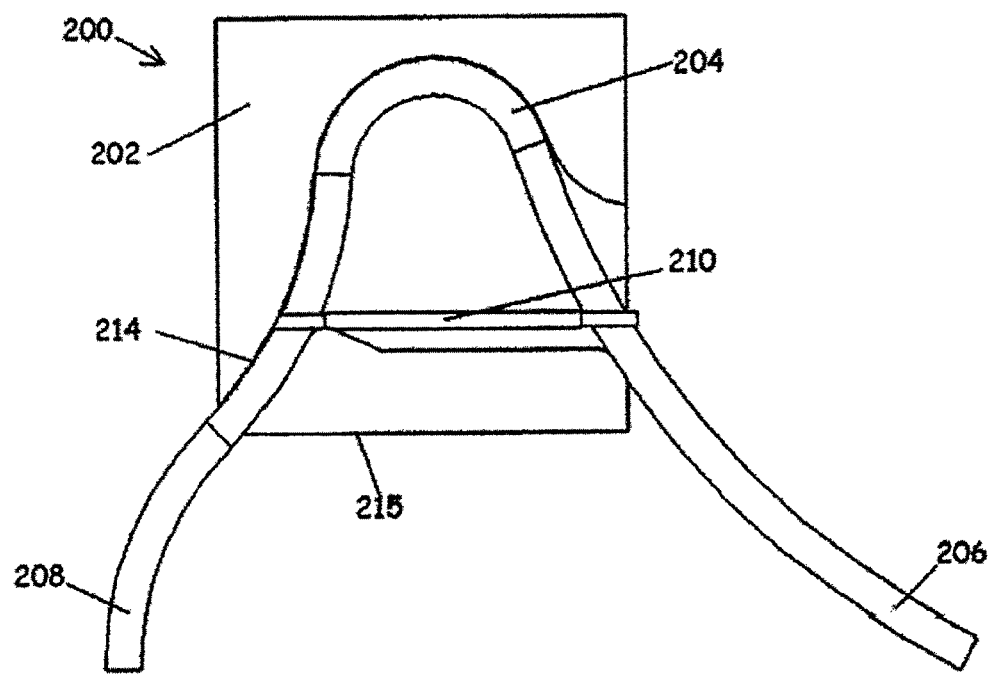
FIG. 2A shows a front view of the tubing and the catheter controller in accordance with one embodiment.

One embodiment of the controller as an elasticized compensating device, herein called the first embodiment 200 is shown in FIGS. 2A-3B. FIG. 2A shows a front view of the first embodiment 200. FIG. 2B shows an exploded view of the first embodiment 200. A base 202, designed to house a flexible tube loop 204 and a tension spring (or elastic member) 210, is molded out of a soft foam rubber or plastic and has an adhesive back surface 216 (FIG. 2B). The tube loop 204 sits in the drainage tube compartment 218. One end 206 (incoming tube) of the tube loop 204 is connected to the external end of the Foley catheter 100. The other end 208 (outgoing tube) of the tube loop 204 is connected to a drainage collection bag. A tension spring 210 bends and holds the tube loop 204 as seen in FIG. 2A. The tension spring 210 and the side of the drainage (or outgoing) tube 208 are attached to the base 202 in section 214. The geometry of section 214, positions the tube loop 204 at an angle relative to the bottom edge 215 of the base 202 that is appropriate whether the leg is straight of bent. Shown in FIG. 2B, this embodiment uses a base 202 that is molded with a curve to fit the contour of the leg, other embodiments might be flexible and would not need to be molded with a curve. A cover plate (or protective shell) 212 is attached to the base 202 (FIG. 2B) creating a housing for the tube loop 204 which allows for the changing of length, while keeping the tube loop 204 and the incoming tube 206 parallel to the body.

Figure 3A:
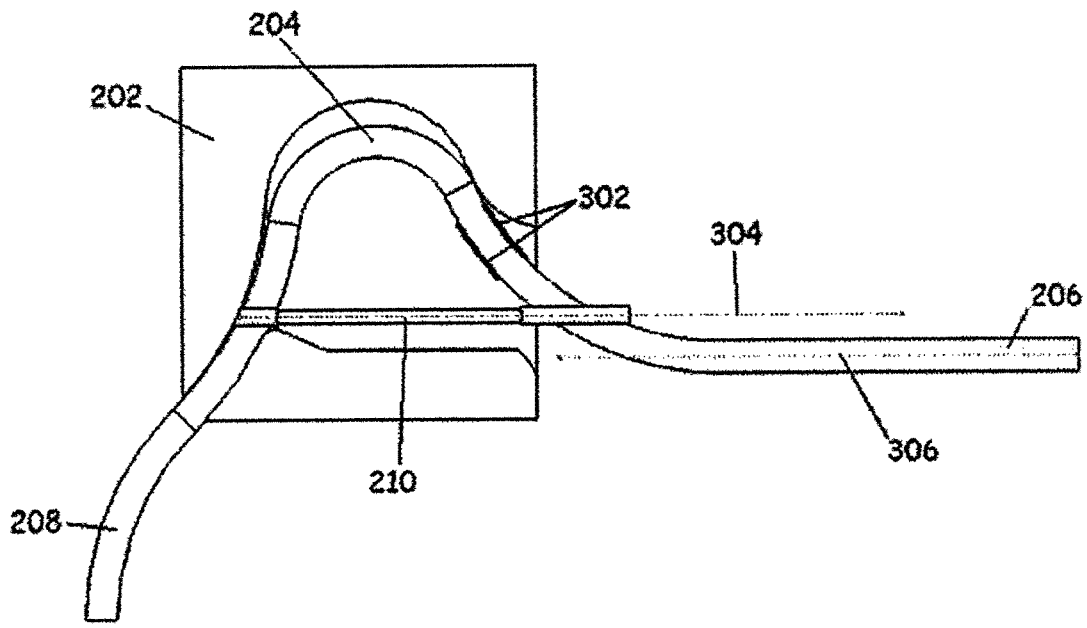
FIG. 3A shows the tubing and the catheter controller with the calibrated force acting on the tension spring in accordance with one embodiment.
Figure 3B:
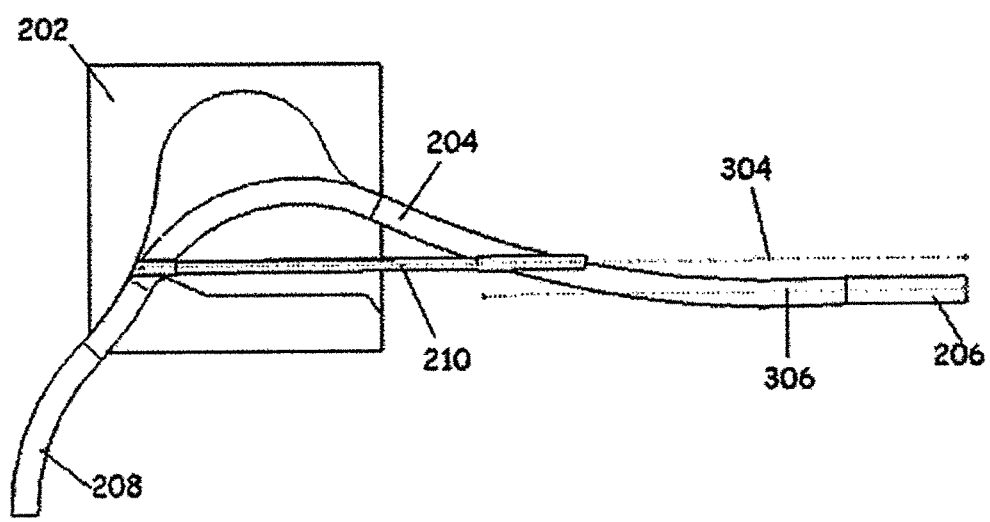
FIG. 3B shows the tubing and the catheter controller with a force greater than the calibrated force, causing the tension spring to lengthen and allowing a greater length of drainage tube.

FIG. 3A shows the first embodiment 200 with a safe predetermined force. "Calibrated force" is defined as the minimum force required to keep a catheter balloon at the bottom of the bladder. The resulting position of the tube loop 204 is in line with pre-marked calibration markings 302. The line of force 304 caused by the tension spring 210, is in line with the direction 306 of the Foley catheter. The calibrated force is that minimal force required to keep the balloon of the catheter at the base of the bladder. FIG. 3B shows the first embodiment 200 with a force greater than the calibrated force acting on the tension spring 210, causing the tension spring 210 to lengthen and allowing a greater length of tube loop 204 to be delivered.

Operation

First Embodiment

Figure 2B:
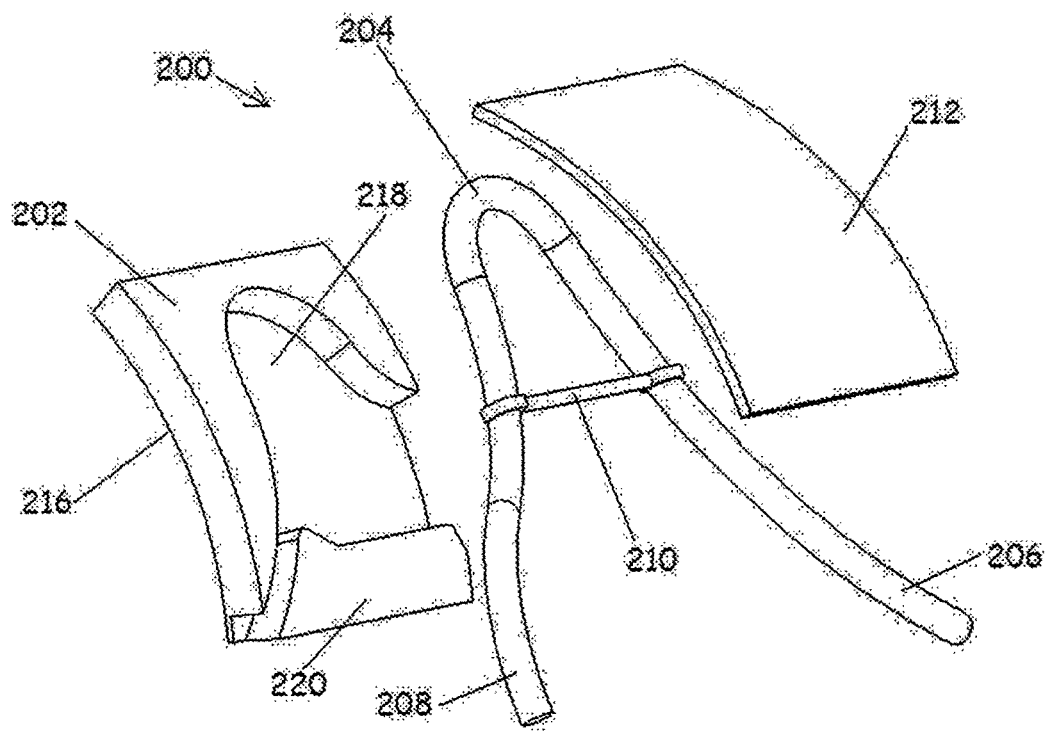
FIG. 2B shows an exploded view the tubing and the catheter controller in accordance with one embodiment.

The catheter controller 200, is attached to the patients leg by means of an adhesive surface 216 on the backside of the base 202 (FIG. 2B). It is orientated such that the end of the drainage (or outgoing) tube 208 points in the general direction of the drainage bag, where it will then be connected. As can be seen by FIG. 2A, the outgoing tube 208 is attached to the base 202 and positioned approximately 45.degree. relative to the bottom edge 215 of the base 202. The 45.degree. angle of the outgoing tube 208 optimally places the outgoing tube 208 such that the maximum amount of bend the outgoing tube 208 will have to undergo is about 45.degree. regardless of the patient's leg position. The incoming tube 206 is connected to the external end of the Foley catheter 100 and is held in constant tension by the tension spring 210, when placed in between the calibration markings 302 shown in FIG. 3A (see method of operation for securing controller below). Shown in FIGS. 3A and 3B, the line of tension 304 of the tension spring 210, is always parallel with the path 306 of the incoming tube 206 and therefore the Foley catheter 100 itself. The tension spring 210 effectively pulls on the catheter 100, with a safe, predetermined force of less than 3 ounces (this force has been calculated to be safe, but is subject to change upon further testing). This calculated force, is distributed over the contact surface between the balloon and the bottom of the bladder, resulting in a surface pressure that will be less than the blood pressure in the blood vessels around the base of the bladder. This predetermined force is strong enough to keep the Foley catheter 100 secure, but not large enough to damage the blood vessels on the bottom of the bladder. By preventing the Foley catheter 100 from moving within the bladder, catheter pistoning is greatly reduced leading to a reduction in patient discomfort as well as lowering the risk of infection. A set of marked calibration lines (or markings) 302 is provided such that the tube can be moved within these lines and the correct amount of tension will be set. This point is where the tension is at its minimum and the distance from the leg attachment point to the catheter is at its minimum. When a force greater than said safe, predetermined force of the tension spring 210, is experienced, such as when the patient's leg is stretched, the tension spring 210 lets out and more drainage tube length is allotted (shown in FIG. 3B). This prevents any force greater than the safe predetermined maximum force, from pulling on the Foley catheter 100 and potentially causing damage to the bladder 104. This configuration constantly keeps a safe tension on the Foley catheter 100 while giving or taking excess lengths of the incoming tube 206 to account for different leg and body movement. The cover 212 creates an enclosed housing for the tube loop 204 which allows for the changing of length, while keeping the tube loop 204 parallel to the body. The cover 212 prevents the tube loop 204 and the tension spring 210 from getting caught on anything, and also creates a desirable low profile for the user, especially when worn underneath clothing.

The method of operation for securing the controller, when the controller is used for catheter tension control, is as follows:

1. Pull lightly on the catheter till the catheter balloon is resting on bladder bottom.
2. Cut incoming tube 206 so that when the catheter connector (not shown), is actually attached to the tube, and when the connector is then connected to the catheter, which is now in its most downward position with the balloon resting on the bladder bottom, the controller will be in a position about ½ to 1 Inch short of the final desired position on the thigh.
3. Slide controller along the thigh until the incoming tubing 206 or tension spring 210 is at the calibration lines 302 and the controller is positioned so that the elastic spring 210, the incoming tube 206 and the catheter are all in a straight line.
4. Remove backing paper and adhere controller 200 to the thigh.

Other Embodiments

Figure 4A:
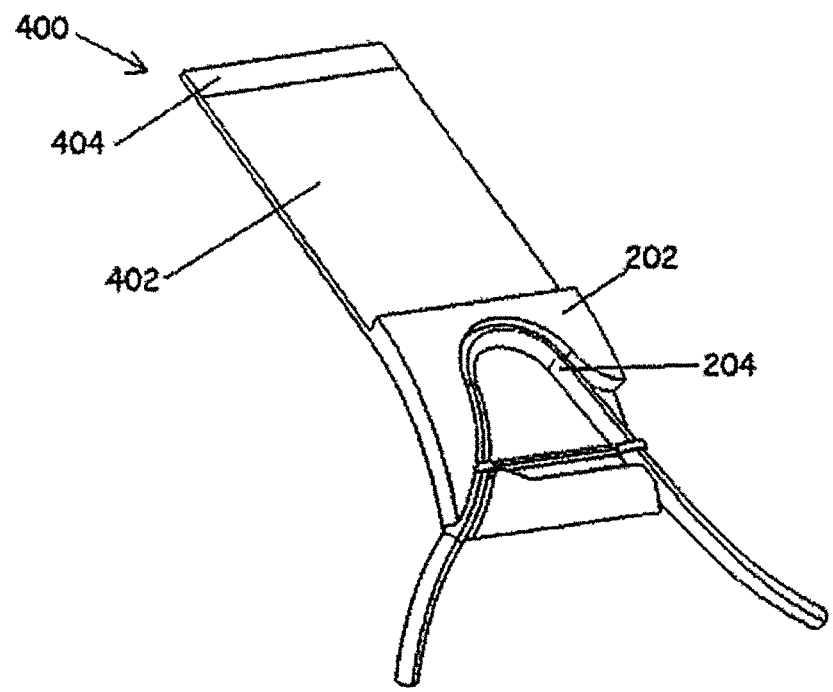
FIGS. 4A and 4B show an alternative embodiment of the controller.
Figure 4B:
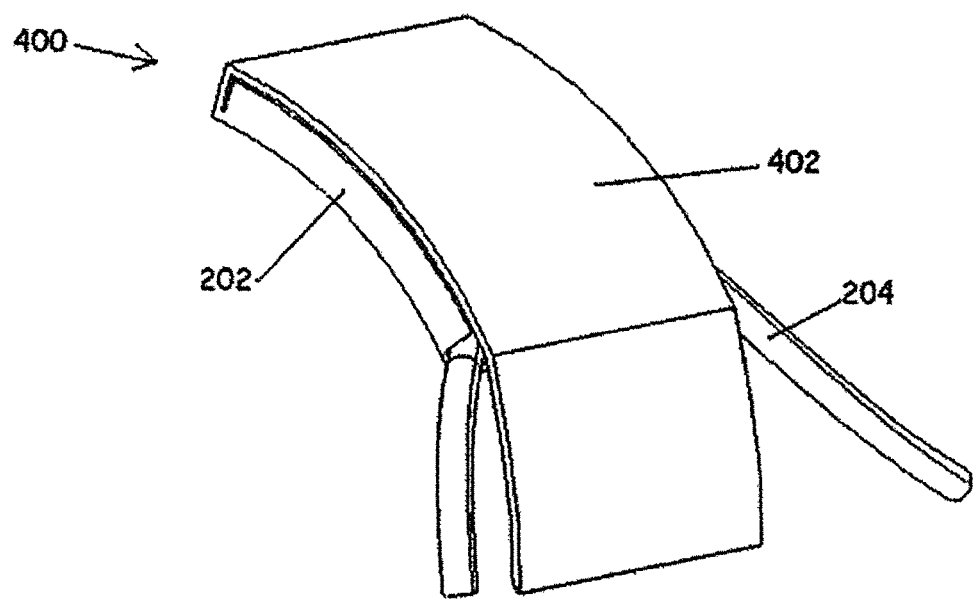

FIGS. 4A and 4B show another embodiment herein called the second embodiment 400. Instead of a cover plate 212, a cover strap 402 is attached to the base 202 and folds over the tube loop 204, and attaches to the patient's leg, or alternatively, to the bottom section of the base 220, using an adhesive placed on one end 404. FIG. 4A shows the second embodiment 400 in the open position and FIG. 4B shows the second embodiment 400 in the closed position.

Figure 5:
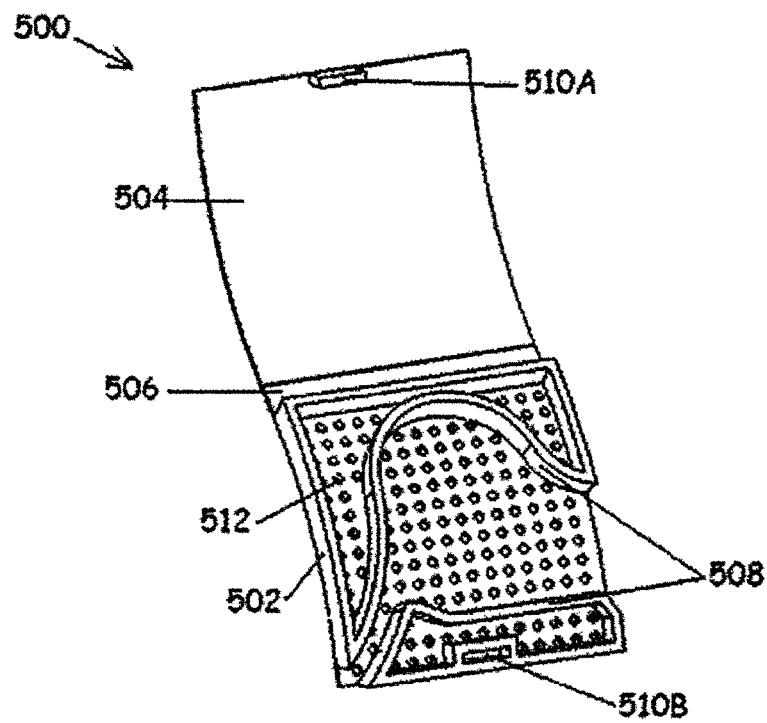
FIG. 5 shows another alternative embodiment of the controller.

FIG. 5 shows another embodiment herein called the third embodiment 500. In this embodiment 500, the base 502 and cover 504 are molded as one piece, joined by a living hinge section 506. The living hinge 506 allows for the cover 504 to fold over and connect to the base 502 through a snap fitting 510A (male) and 510B (female). The drainage tube compartment 218 shown in FIG. 2B is replicated in this embodiment 500 by molded walls 508. A predetermined hole pattern 512 is molded into the bottom surface of the base 502. This hole pattern 512 allows the skin to breath while the controller is attached, and serves as an adhesive release aid as adhesive solvent can be applied through the holes 512 and onto the skin.

Figure 6:
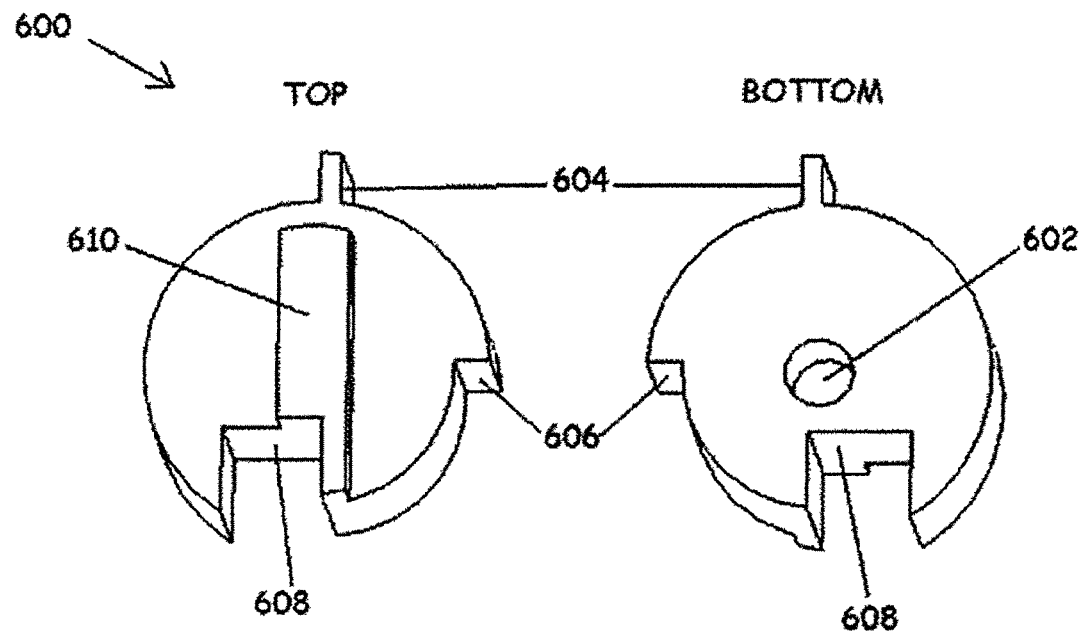
FIG. 6 shows top and bottom views of an adjustment dial in accordance with one embodiment.
Figure 7:
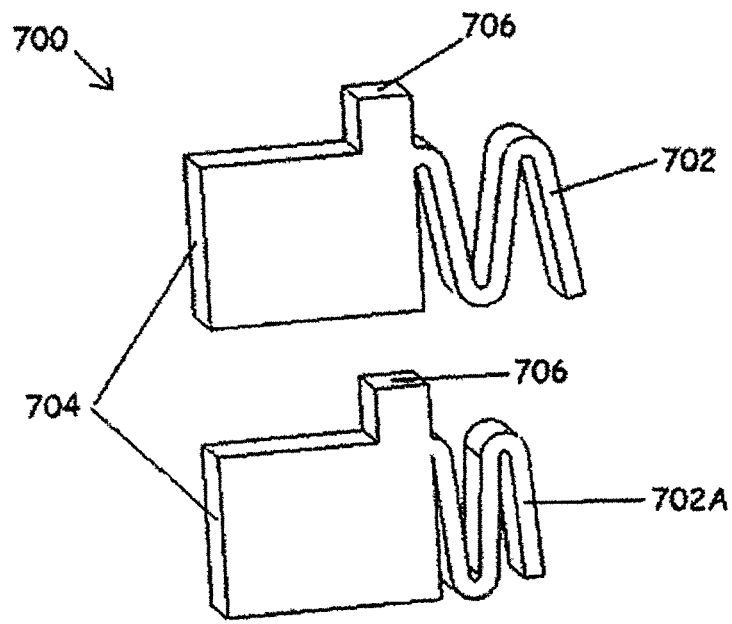
FIG. 7 shows a spring loaded slide with the spring un-compressed and with the spring compressed in accordance with one embodiment.

Another embodiment may include a means for adjusting the tension of the tension spring 210. This can be accomplished by a number of methods. One such method uses a rotatable dial 600 shown in FIG. 6, a spring loaded slide 700 shown in FIG. 7, and a modified base 800 shown in FIG. 8. As shown in FIG. 6, the dial 600 has a recess for a mounting post 602, an attachment point 604 for the tension spring 210, a recess 606 for the slide 700, when the tension spring 210 is at the lower tension setting, and a recess 608 for the slide 700, when the tension spring 210 is at the higher tension setting. Ideally, the lower tension setting provides just enough tension to keep the tube loop within the device.

The higher tension setting is used when the device is employed to maintain a constant minimum tension on the catheter. In the latter case, there is the possibility for the doctor or the patient to remove the constant tension on the catheter if the constant tension creates a problem. A dial handle 610 is also provided to aid in the rotation of the dial 600. Shown in FIG. 7, the slide contains a molded compression spring section 702, (shown compressed as 702A), a front section 704 which fits into the recesses 606, and 608, of the dial 600, and a slide handle 706 to aid in the movement of the slide 700.

Figure 8:
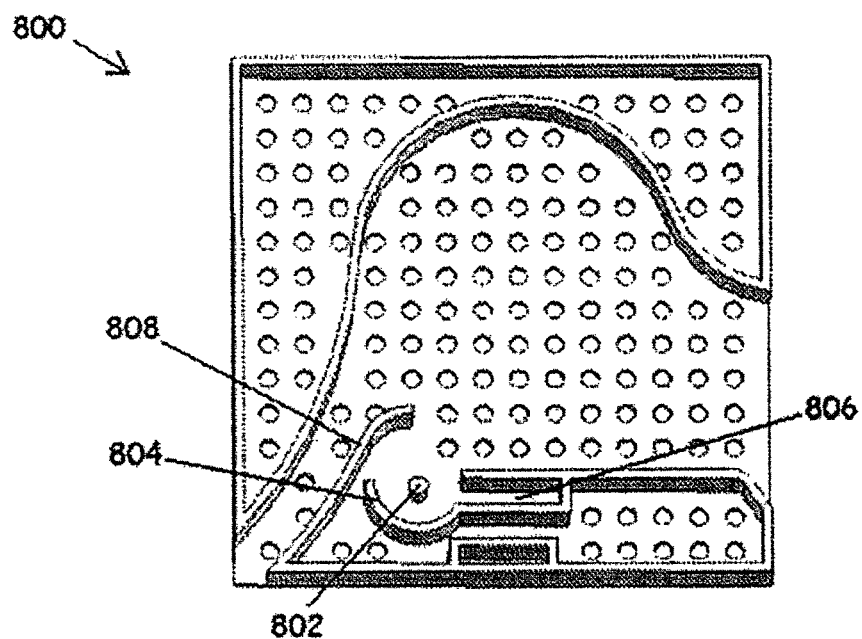
FIG. 8 shows a base with a dial mounting post and recesses for the dial and slide in accordance with one embodiment.
Figure 9A:
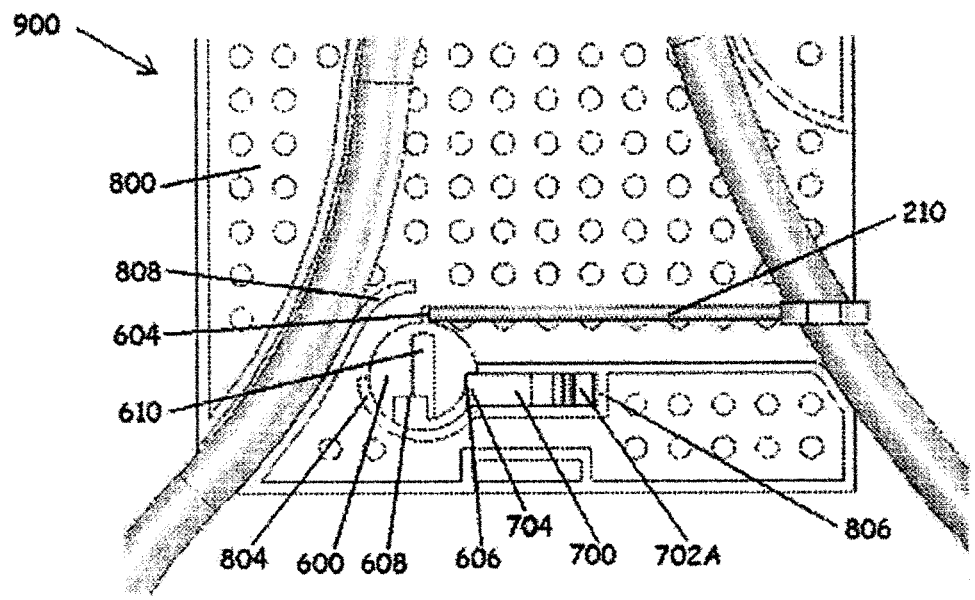
FIG. 9A shows a front view of an alternative embodiment with a means for adjusting the tension of the tension spring in the un-tensioned position.
Figure 9B:
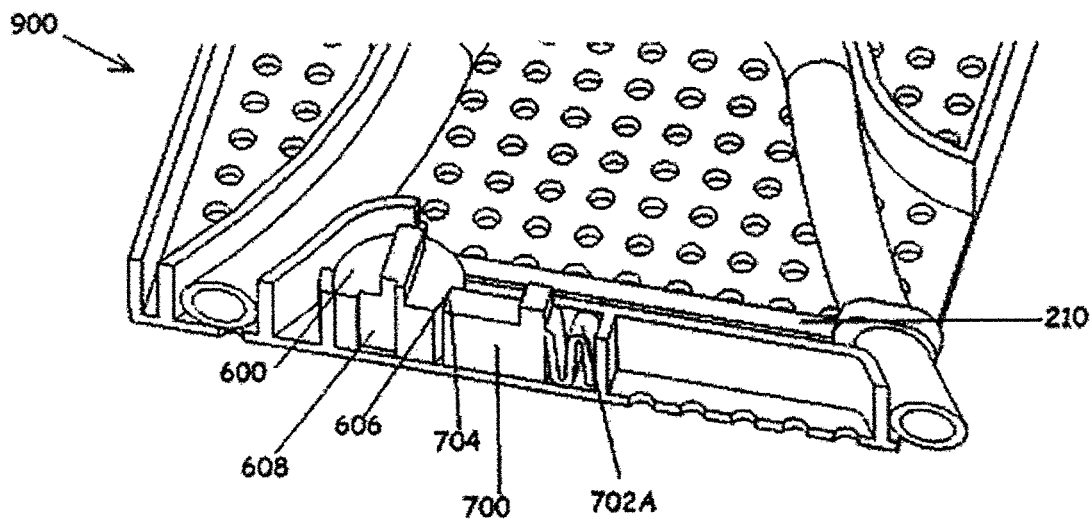
FIG. 9B shows a cross-section view of one embodiment with a means for adjusting the tension of the tension spring in the minimum-tensioned position.
Figure 10A:
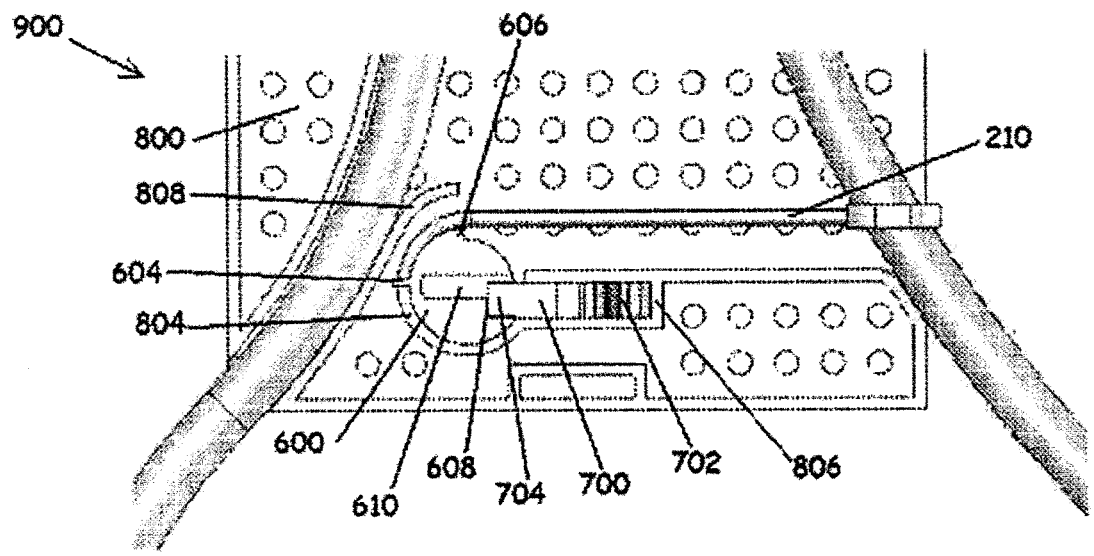
FIG. 10A shows a front view of an alternative embodiment with a means for adjusting the tension of the tension spring in the tensioned position.
Figure 10B:
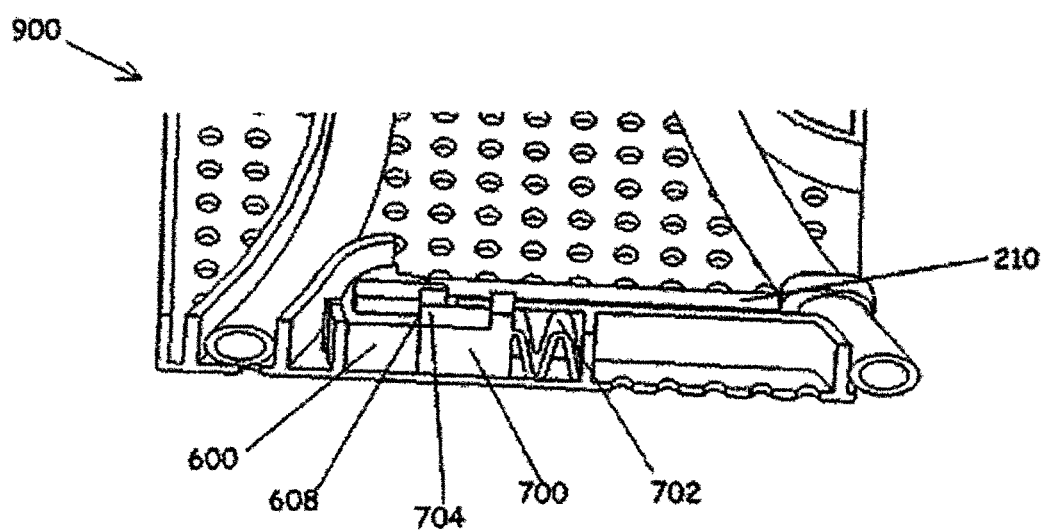
FIG. 10B shows a cross-section view of one embodiment with a means for adjusting the tension of the tension spring in the tensioned position.
Figure 11A:
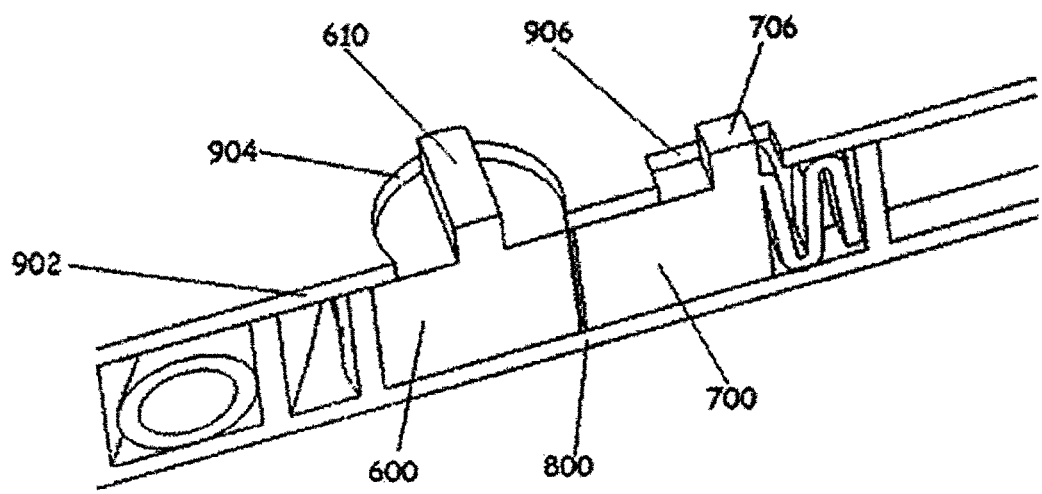
FIG. 11A shows a cross-section view of one embodiment with a means for adjusting the tension of the tension spring and with a cover plate.
Figure 11B:
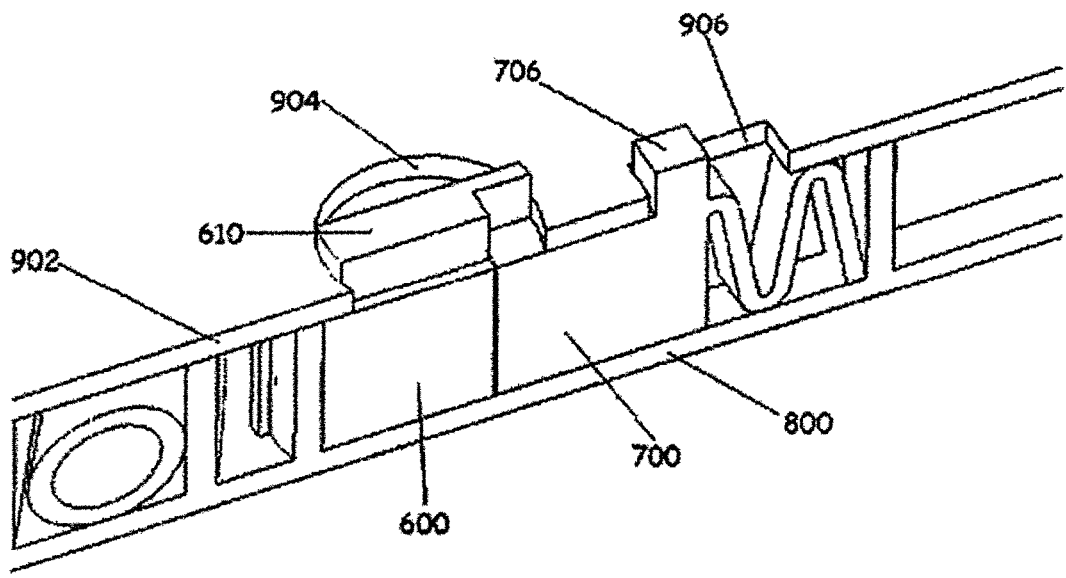
FIG. 11B shows a cross-section view of one embodiment with a means for adjusting the tension of the tension spring in the tensioned position.

Shown in FIG. 8, the base 800, contains a mounting post 802 for the dial 600, a dial compartment 804, a slide compartment 806, and a rib 808 for preventing the tube loop 204 from contacting the tension spring 210, and as an aid in reducing any possibility of kinking. FIGS. 9A-11B, show the completed assembly of the adjustable embodiment 900. FIG. 9A shows this embodiment 900 in the low tension position. The tension spring 210, attaches to the surface 604 of the dial 600. The dial 600 is placed in the dial recess 804 of the base 800 such that the mounting post 802 fits into the mounting post recess 602. The slide 700, sits in the slide compartment 806, of the base 800. In the lower tensioned position, the front section 704 of the slide 700 rests against recess 606 of the dial 600 and prevents any clockwise rotation of the dial 600. In this position (FIG. 9A), the compression spring 702A of the slide 700, is compressed. The attachment point 604 of the tension spring 210 to the dial 600 is in the vertical position, meaning no tension is being applied. FIG. 9B shows a cross-section view of the adjustable embodiment 900 in the un-tensioned position. FIG. 10A shows the adjustable embodiment 900 in the tensioned position. The dial 600 has been rotated 90.degree. counter clockwise, causing the tension spring 210 to elongate and thus be in the higher tension mode. With the dial 600, rotated into this position, the slide 700 is pushed forward by the slide's compression spring 702, and rests in the tensioned recess 608 of the dial 600. The front section 704 of the slide 700 prevents any further rotation of the dial 600. FIG. 10B shows a cross-section view of the adjustable embodiment 900 in the tensioned position. FIGS. 11A and 11B show cross-sections of the adjustable embodiment 900 with a cover 902 in the closed position. FIG. 11A shows the embodiment 900 in the lower tensioned position, while FIG. 11B shows the embodiment 900 in the higher tensioned position. A recess 904 in the cover 902 allows for the dial handle 610 to protrude through when the cover 902 is closed. A similar recess 906 is provided for the slide handle 706. This configuration, allows the user to adjust the tension of the tension spring 210 without having to open the cover. By pushing the slide 700 to the right using the slide handle 706, the dial 600 is now able to be rotated using the dial handle 610 and tension can either be applied or alleviated.

Figure 12:
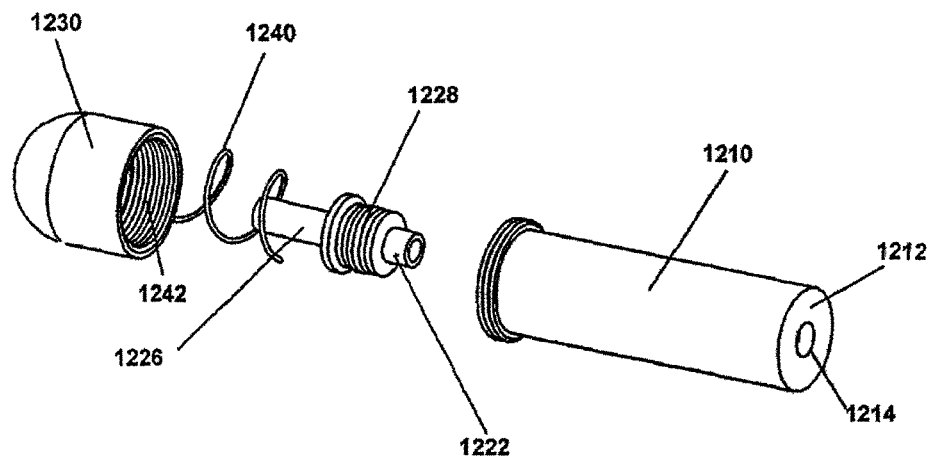
FIG. 12 shows another embodiment that would allow for compensating tube path length changes, while also providing a means to keep a low adjustable tension on the catheter.
Figure 13:
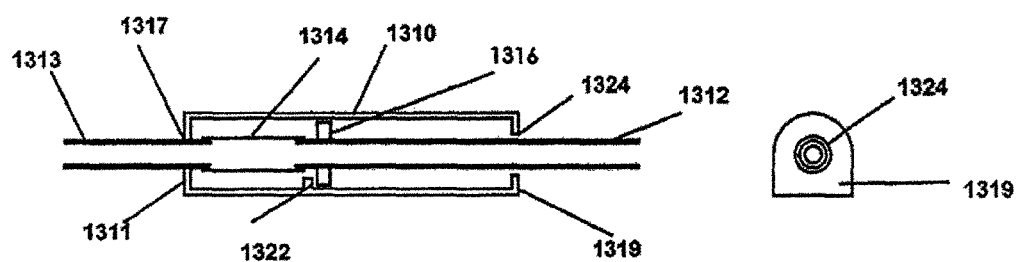
FIG. 13 shows another embodiment that utilizes a controlled thin wall elastomer type of tube in a protective shell that provides a smooth continuous path for the fluid while allowing for tube length compensation as well as a continuous low tension pull on the catheter.

An example of yet another embodiment is shown in FIG. 12. This device provides a means of adjustment to finely control the degree of force produced by the tubing before the tube lengthens or contracts as a result of leg movements. Container 1210 provides protection for the expandable tubing (or elastic member) 1228 and provides a place of attachment to the thigh. The attachment may be direct by means of an adhesive. The container would also prevent the flexible area from bending and collapsing on itself thereby restricting flow to the collection bag.

Providing a pivoting means for the container, preferably lockable, that allows the container to pivot in order to reduce the binding friction on the tubing when the pull is other than in a straight up or down direction. The pivot may be ball shaped to give a degree of movement in all directions. This type of lockable pivot is commercially available.

Container 1210 is a hollow tube, with a tube bottom 1212, that has a hole 1214 thru which outgoing tube 1222, located at the lower end of elastic member 1228 passes through and is attached to container 1210 at the hole 1214.

Elastic member 1228 is shown with a bellows type section that provides the expansion in this case. The incoming tube 1226 passes freely thru a hole in cap 1230. Cap 1230 has a threaded section 1242 running down most of its interior length that engages with the threaded section at the top of container 1210.

Spring 1240, which has a smooth finishing coil at both ends that catch under projections on the expansion unit and projection on the cap unit.

Other embodiments may be used as a method for controlling any other tubing system where expansion and contraction are of concern. By forming a loop, attaching an elastic means across the base of the loop, attaching one end of the elastic loop with the tube attached to the securement point desired, and covering the loop with a sheet of material, the tubing system is constantly in tension, and is kept parallel to the body part, but not close enough to inhibit movement of the tube as the loop expands and contracts. This covering can be anything from a fabric loosely spread over the loop and taped to the body to a sheet of material mounted in such a way as to be parallel to the body but spaced a distance away that does not inhibit the tubing movement as it expands and contracts.

It should be noted, that the bellows section of the expansion unit could be replaced with a section of coiled tubing instead. In this case provision would be made for a projection at a point onto just above the coiled section on the upper tube onto which the spring could grasp.

The ideal arrangement would have the outer tube adjusted to a height that provides enough springiness to just support the tubing above or around it so that any movement, in any direction can be absorbed by the unit and not transmitted to the catheter. The best arrangement would depend on the materials employed and the exact configuration. The most likely configuration would involve the accordion or accordion thread configuration as the outside tube since it would yield the best stability with the greatest flexibility. It should be noted that a coiled tube within the container could provide this type of flexibility, but would be more difficult to control with a spring in an adjustable manner.

There is also the possible advantage that an accordion shaped compensatory section would help in the retardation of bacterial film growth within the tubing because of intermittent flow and the resulting flush action. Compare this to a smooth inner wall and a small continuous flow and the possible increased rate of bacterial film growth when given a continuous path.

Another embodiment is described in U.S. provisional patent application No. 61/478,566 filed Apr. 25, 2011

There are many situations where a continuous tubal path for a liquid or gas is required, such as urinary catheter drainage, IV catheter fluid insertion, etc. In many of these cases a method that would compensate for changes in the tube path length and/or some form of tensioning control would be a very desirable feature. In some medical applications it could be life-saving. Ideally, the tube should be continuous with a smooth interior fluid path and provide a high degree of extension with a low tensile force. The overall profile should be low with a minimum of projections to reduce chance of entanglement as well as to ensure comfort for the patient. It must be robust enough so that fluid flow will not stop if pressure exerted on outside of tube.

Embodiment with Thin Wall Stretchable Tube

The embodiments described in FIGS. 13A-15 describe a continuous stretchable tubal path that has a high degree of extension at very low tensile forces by means of utilizing the elasticity of a very thin wall, easily collapsible elastomer or rubber like tube as part of the tubal path. It is accomplished by providing means to do the following:

a. Protecting the thin wall section from outside pressures
    b. Never allowing the elastomer tube to become shorter in length than its natural length when under no tension
    c. Never allowing the elastomer tube from stretching beyond its breaking length
    d. Never allowing the elastomer tube from twisting An example of the practical use for such a device would be as a part of a urinary catheter security device such as the one described in U.S. provisional patent application No. 61/359,912. One need only to add a means of securing such a device to the thigh and the fittings necessary to attach the tubing to the urinary catheter on the one end and the tube leading to the collection bag on the other in order to get the conditions necessary to stabilize a urinary catheter. This arrangement would have many advantages over the methods described in provisional patent application No. 61/359,912.

A further application would be to incorporate such an arrangement as applied to an IV catheter between the catheter and the medical tube feeding the IV. In such a case, the IV catheter would be fastened down after insertion and the tubing fastened down at a point in line with the catheter, with or without a slight degree of tension on the IV site. The application of a tension factor would reduce the degree of skin movement resulting in less needle movement within the vein. The stretch component would reduce the strain on the IV catheter if the medical tube or the secondary attachment point of the tube were disturbed. This action would isolate the tube movement from the catheter thereby reducing the chance of the catheter either being dislodged or causing damage to the vein or bladder or most any body part a catheter may be employed.

The remaining figures provide possible ways to satisfy the above identified conditions. The incoming tube 1312 is glued to elastic tube (or elastic member) 1314 on one side. The other side of the elastic tube is glued to exiting (or outgoing) tube 1313, which passes through outer shell exiting end hole. The incoming tube 1312 is glued to hole in slider 1316, and is free to slide thru exiting hole 1324. The incoming tube 1312 is free to slide thru outer shell incoming cover end 1319. Slider 1316 slides freely within outer shell 1310. The "D" shape of slider 1316, within the D shape of outer shell 1310 will prevent any twisting of elastic tube 1314. Outer shell incoming end 1319 prevents slider 1316 from any further outward movement thereby protecting elastic tube 1314 from over stretching. Maximum slider stop projection 1322 prevents slider 1316 from moving any closer to outer shell exiting end 1311, thereby insuring the minimum length condition needed to maintain elastic tube 1314 shape.

This arrangement has the outer tube protecting the elastic tube from outside pressures as well as providing an environment where the elastic tube cannot be collapsed by shortening to below its natural length, stretched to its breaking point or twisted out of shape. The result is an elastic tube that is always open to provide a clear path for any fluid to pass through.

Shows an extension or telescoping tube variation. With this arrangement, the elastic tube (or elastic member) 1414 could be longer if desired without increasing the size of the device. This longer elastic tube will give a greater extension with a softer pull. This, together with the telescoping action, will result in less stress on the bladder as well as on the elastic tube in a device that is shorter and easier to manage. The actual stretch could equal the length of the elastic tube, which is about equal to the outer tube 1410 length. Another feature uses the pin 1450 through hole 1418 to keep slider 1416 from moving toward the incoming end. Removing pin 1450 and freeing slider 1416 to move to stop 1442, will remove the initial constant tension component. This allows for adjustment and/or safe removal of tension during actual use by the nursing staff or by the patient.

Figure 14A:
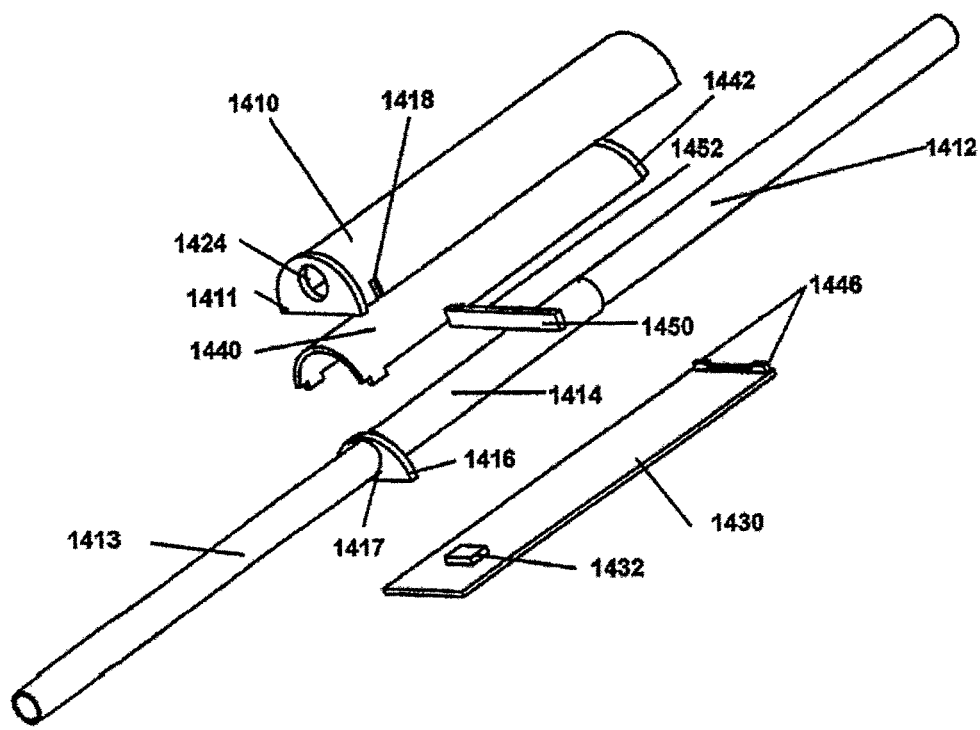
FIGS. 14A, 14B, and 14C show a device similar to FIG. 13, but with the added feature of an enclosed telescoping inner shell. This arrangement allows for greater tube length compensation for the same size device as well as a means to easily remove the constant tension feature without professional help.

FIG. 14A shows an exploded view of a controller that has provision for adjusting or removing the tension on elastic tube 1414 as well as a telescoping shell arrangement that allows for greater stretch in a shorter device.

Outgoing tube 1413 is glued to slider 1416 and then to elastic tube 1414, which is glued to incoming tube 1412. Tube 1412 is glued to inner shell incoming hole 1444 (as shown in FIG. 14C) in inner shell back plate 1442 is glued to the incoming end of inner shell 1440.

Figure 14B:
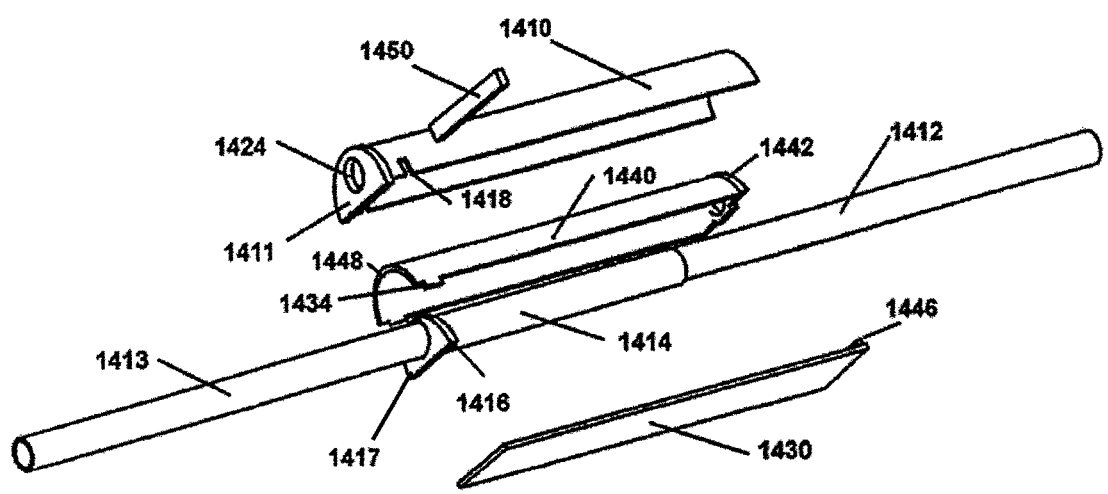

FIG. 14B shows the same exploded view as 14A, but from an opposing view.

Figure 14C:
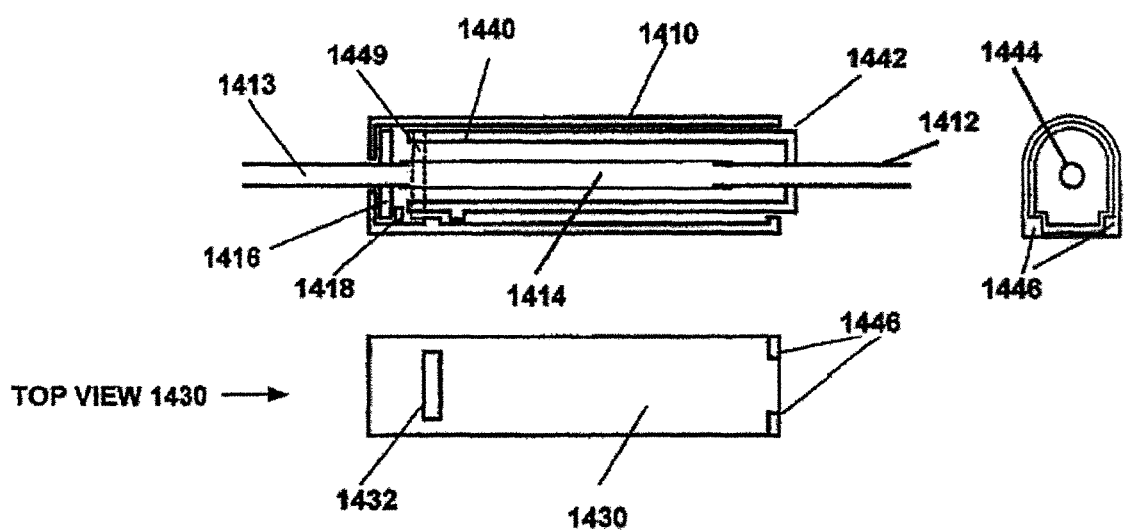

FIG. 14C shows a cross-section of the controller fully assembled. Exiting (or outgoing) tube 1413 slides freely in exiting hole 1424. Initially slider 1416 is restrained from moving within outer shell 1410 by safety pin 1450. Pin 1450 is held in place by raised projections 1452. These projections on safety pin 1450 are not high enough to prevent the pin-1450 from being removed from the entry holes on both sides of outer shell 1410 with a little additional force. The removal of the pin would allow slider 1416 to move over to secondary position 1449, shown as a dotted outline in FIG. 14C, and is stopped from moving any further be slider stop 1432, which is located on the outer shell bottom plate or base 1430. This movement is enough to remove the minimum tension employed when the device is used to maintain a minimal tension as described in U.S. provisional patent application No. 61/359,912. When used in this position, safety pin 1450 could be reinserted to prevent the slider from moving back toward the exiting end. To prevent the elastic tubing from stretching to its breaking point as well as to prevent the inner shell from exiting out of the outer shell, inner shell maximum movement stop 1446 acts against inner shell stop 1434. Inner shell back plate 1442 is fastened to the incoming end of inner shell 1440. The inner shell leading edge-1448 against slider 1416 acts as the limiting condition for maintaining a minimum length of elastic tube 1414.

The elastic tube 1414 was dip molded out of a two part elastomer made by "Smooth-on" named Dragon Skin Q. In this case the tube was plain, but it would be possible to provide special benefits if lateral and/or longitudinal ribs were molded in at the same time. The tube can be made of any suitable rubber like product.

Figure 15A:
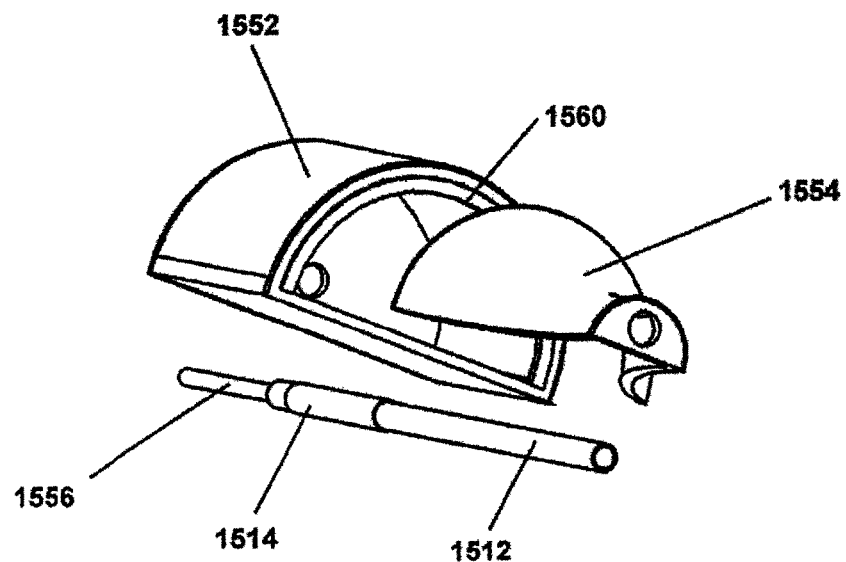
FIGS. 15A and 15B show an embodiment of the same concept as applied to an IV Catheter.
Figure 15B:
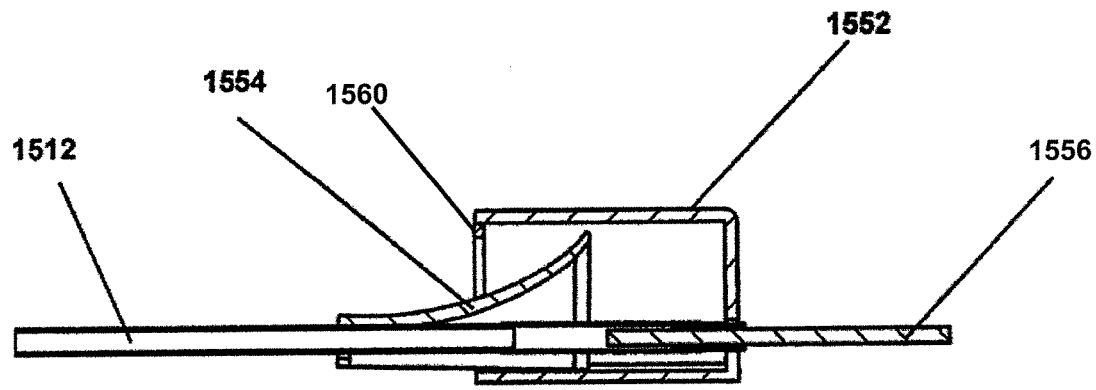

In one special variation of the device, the benefits of the flexible, stretchable feature can be applied to an IV device, as shown in FIGS. 15A and 15B. In this case, the inner shell 1554 is shaped as shown to allow for more lateral movement of the incoming tube 1512 and better isolation of any incoming tube disturbance from affecting the IV needle position within the vein. In this case, the elastic tube 1514 would benefit if it had some small ribs for the short distance at the bending end. Since the rest of the tube would be of the same cross section, near maximum stretch would still be possible. The tension aspect of the device could cause a contraction of the skin between the IV site and the secondary tube attachment site. This contraction causes a significant reduction in skin movement at the IV site, and therefore results in less needle movement within the vein. The secondary tube attachment site could be a device such as the "Site-saver," or any other method of securing the incoming tube at a point before it reaches the IV site. The secondary site is often used to reduce the strain resulting from outside tubal movement from affecting the IV needle site. As an added benefit, the flat underside of the IV outer shell 1552 enables the needle to be in a more parallel position relative to the skin, and therefore less likely to pierce the vein if disturbed. The larger area of the flat surface also lends itself to a more secure attachment zone, especially if a Velcro solution were to be employed.

FIG. 15A shows an exploded view of an IV model that is yet another application of the same concept. In this case inner shell 1554 is shaped to allow much greater lateral movement. Outer shell 1552 fastened to IV needle/catheter 1556 and IV needle/catheter 1556 is attached to elastic tube 1514, which is attached to the medical tubing 1512. The other end of elastic tube 1514 is attached to incoming tube 1512 as well as inner shell 1554. Inner shell flare is designed to spread contact points of inner shell 1554 against elastic tube 1514 when in extreme lateral positions of the incoming tube.

FIG. 15B shows a cross-section of IV model.

Those of skill in the art will recognize certain modifications, permutations, additions and sub-combinations thereof of parts noted herein. While a device or an accompanying method have been described for what are presently considered the exemplary embodiments, the invention is not so limited. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

This arrangement has the outer tube protecting the elastic tube from outside pressures as well providing an environment where the elastic tube cannot be collapsed by shortening to below its natural length, stretched to its breaking point or twisted out of shape. The result is an elastic tube that is always open to provide a clear path for any fluid to pass through.

I claim:

1. A control device for a medical catheter, the control device comprising:
    a housing; and
    an elastic member to connect the housing to a tube configured to conduct fluid to or from a patient's body;
    wherein the control device is configured to be secured to a securement point at the patient's body;
    wherein the elastic member is arranged to apply a tensile force to the tube and to elongate and contract in response to relative movement between the housing and the tube to limit the tensile force on the tube to a predetermined safe force, while maintaining tension on the catheter to keep a catheter balloon at the bottom of the patient's bladder.

2. The device of claim 1, wherein the tube has a flexible curved portion and the elastic member comprises a tension spring coupling legs of the flexible curved portion.

3. The device of claim 2, wherein one of the legs of the flexible curved portion of the tube is connected to the housing and another of the legs of the flexible curved portion of the tube is connected to the elastic member, the control device further comprising a dial connected to the housing and connected to the elastic member, the dial being rotatable into a higher-tension position that elongates the elastic member with respect to a lower-tension position of the dial, so as to allow changing tension on the tube without changing a position of the housing on the patient's body.

4. The device of claim 2, wherein the housing comprises a base and a strap attached to the base, the base configured to receive the flexible curved portion of the tube therein, the strap foldable over the base and the flexible curved portion of the tube therein.

5. The device of claim 2, wherein the housing comprises a base and an integral cover, the base configured to receive the flexible curved portion of the tube therein, the cover foldable over the base and the flexible curved portion of the tube therein.

6. The device of claim 1, wherein the elastic member comprises a coil spring connecting the housing to an expansion unit located inside the housing, the tube being connected to a patient-end of the expansion unit, the medical catheter further comprising another tube connected to an end of the expansion unit opposite the patient-end, the expansion unit movable within the housing against the coil spring.

7. The device of claim 1, wherein the elastic member comprises an elastic portion of the tube, the elastic portion having a thinned wall, the elastic portion located inside the housing.

8. The device of claim 7, wherein the elastic member is protected from one or more of crushing, twisting, foreshortening, and over-extending to a breaking point, so as to maintain a continuously open path for drainage from the patient's bladder to a drainage bag.

9. The device of claim 7, wherein the housing comprises telescopic shells, and the elastic portion is located within the telescopic shells.

10. The device of claim 9, wherein an inner shell of the telescopic shells has a shape that narrows from a point within an outer shell of the telescopic shells to a point outside the outer shell and located at a patient-end of the medical catheter.

11. The device of claim 1, wherein the predetermined safe force is defined as a force that allows a balloon of the catheter to exert a pressure on a bottom interior of the patient's bladder not exceeding the pressure in capillaries at an area of contact of the balloon to the bottom interior of the patient's bladder.

12. A control device for a medical catheter, the control device comprising:

a housing; and an elastic member to connect the housing to a tube configured to conduct fluid to or from a patient's body;

wherein the control device is configured to be secured to a securement point at the patient's body;

wherein the elastic member reduces movement of the medical catheter by compensating for movement of the control device by elongating and shortening thus reducing pistoning of the catheter, reducing damage to bodily tissues and reducing a risk of infection, the elastic member maintains a direction of pull substantially constant and substantially maintaining a tensile force not exceeding a safe maximum tensile force on the medical catheter, and the control device being attached to the securement point at the patient's body isolates the catheter from any pulls on an outgoing portion of the tube.

* * * * *